United States Patent [19]

Lesieur et al.

[11] Patent Number: 5,179,091
[45] Date of Patent: Jan. 12, 1993

[54] CHALCONES

[75] Inventors: Daniel Lesieur, Gondecourt; Daniel H. Caignard, Paris; Isabelle Lesieur, Gondecourt; Michelle Devissaguet; Béatrice Guardiola, both of Neuilly Sur Seine, all of France

[73] Assignee: Adir Et Compagnie, Courbevoie, France

[21] Appl. No.: 709,613

[22] Filed: Jun. 3, 1991

[30] Foreign Application Priority Data

Jun. 22, 1990 [FR] France .................. 90 07813

[51] Int. Cl.$^5$ .................. A61K 31/54; C07D 279/08; C07D 279/14; C07D 265/14
[52] U.S. Cl. .................. 514/224.5; 514/228.2; 514/229.8; 514/230.5; 514/231.5; 544/54; 544/55; 544/58.4; 544/58.5; 544/60; 544/89; 544/92; 544/96; 544/101; 544/105
[58] Field of Search .................. 544/54, 55, 58.5, 60, 544/89, 92, 96, 101, 105; 514/224.5, 228.2, 229.8, 230.5, 231.5

[56] References Cited

U.S. PATENT DOCUMENTS 4,778,792 10/1988 Lesieur et al. .................. 544/101

OTHER PUBLICATIONS

Farmdoc Alerting Bulletin for Aug. 5, 1975, Section B Pharmaceuticals, cover sheet plus p. 8 Abstracting French 73/023,281 (published No. 2 244 507) corresponds to French Application No. 73/23281.
Farmdoc Alerting Bulletin for Jul. 23, 1986 Section B Pharmaceuticals cover sheet plus p. 15 Abstracting JP 84/210265 (J61/087,650).
Chemical Abstracts Search Reports (CAS) identifying compounds in JP 86/87650 and Questal formula sheets showing the formulas of all compounds disclosed in JP 86/87650 pp. 2 through 8 (claimed compounds) and pp. 2 through 9 (starting compounds and claimed compounds) (address p. 1 only have been removed).
Farmdoc Alerting Bulletin for Jul. 8, 1987 Section B Pharmaceuticals cover sheet plus p. 17 Abstracting EP 0 223 674 (corresponds to French 85/015595 and U.S. Pat. No. 4,778,792).
Moussaviet Chemical Abs. 111(19)174049Y, 1989 Eur. J. Med. Chem. 24(1), 55–60.

Primary Examiner—Mukund J. Shah
Assistant Examiner—Y. N. Gupta
Attorney, Agent, or Firm—Gordon W. Hueschen

[57] ABSTRACT

Compounds of general formula (I): in which:

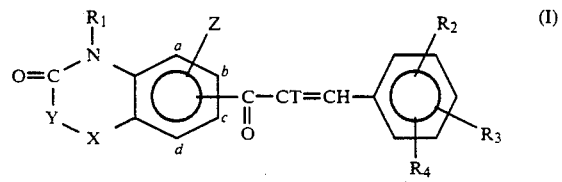

$R_1$, X, Y, Z, T, $R_2$, $R_3$ and $R_4$ are defined in the description. Medicinal products.

18 Claims, No Drawings

CHALCONES

The present invention relates to new heterocyclic chalcones, to a process for preparing these and to pharmaceutical compositions containing them.

Some heterocyclic chalcones have already been described in Patent FR 73/23,281 and in Eur. J. Med. Chem. 1974, 9, (5), 497-500 as having analgesic properties.

More recently, European Patent Application 0,223,674 claims benzoxazinone chalcones having hypolipidemic, analgesic, anti-inflammatory, antimicrobial, antifungal and cardiovascular properties and properties affecting the central nervous system. Patent Application JP 61/087,650 claims chalcones, in particular benzoxazolyl chalcones, endowed with antiallergic properties.

The Applicant has now discovered heterocyclic chalcones which, while retaining good anti-inflammatory properties, are at the same time endowed with exceptional antioxidant properties which are not mentioned in the prior art. The antioxidant properties are closely linked to the novel structure of the compounds of the invention, since the products of the prior art, mentioned above, which are structurally closest to the products of the invention are devoid of them.

More specifically, the invention relates to compounds of general formula (I):

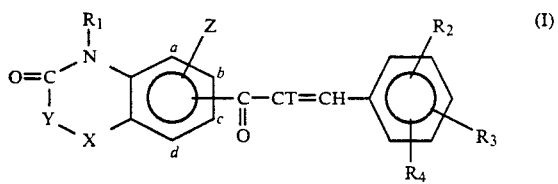

in which:

$R_1$ represents a hydrogen atom or a lower alkyl radical,

X represents:
- an oxygen or sulfur atom,
- a $CH_2$ group, on condition that, in this case, Y represents an oxygen or sulfur atom, Y represents:
- a single bond or a group $CR_7R_8$, where $R_7$ and $R_8$, which may be identical or different, represent, independently of one another, a hydrogen atom, a lower alkyl group, a phenyl group, a substituted phenyl group, a phenylalkyl group or a substituted phenylalkyl group,
- an oxygen or sulfur atom, on condition that, in this case, X represents a $CH_2$ group, Z represents either a hydrogen atom, and in this case T also represents a hydrogen atom, or Z forms with T a link —$(CH_2)n$—$CH(E)$— or $(CH_2)_n$—$CH(CH_2E')$ with n an integer equal to 0, 1, 2 or 3, on the understanding that, in this case, Z is carried by a carbon adjacent to the carbon carrying the acyl group, and E or E' represents a hydrogen atom, a lower alkyl group or a phenyl, heteroaryl or substituted phenyl or substituted heteroaryl group, the term substituted in relation to the terms phenyl and heteroaryl and phenylalkyl in the definition of $R_7$ and $R_8$ and E and E' meaning that these groups may be substituted with one or more substituents selected from lower alkyl, lower alkoxy, halogen, trifluoromethyl or hydroxyl, $R_2$, $R_3$ and $R_4$, which may be identical or different, represent, independently of one another, a hydroxyl or lower alkoxy group or a lower alkyl group, their enantiomers, epimers and diastereoisomers as well as, when $R_1$ represents a hydrogen atom Or when at least one of the groups $R_2$, $R_3$ and $R_4$ represents a hydroxyl group, their addition salts with a pharmaceutically acceptable base, on the understanding that lower alkyl or lower alkoxy is understood to mean linear or branched groups comprising from 1 to 6 carbon atoms, and that heteroaryl is understood to mean unsaturated mono- or bicyclic groups comprising from 5 to 12 atoms other than hydrogen and including in a carbon skeleton from 1 to 3 hetero atoms selected from nitrogen, oxygen and sulfur.

Among bases which may be added to the compounds of formula (I) to form an addition salt, sodium, potassium and calcium hydroxides, or organic bases such as diethylamine, diethanolamine, triethylamine, benzylamine, dicyclohexylamine and arginine, or alkali metal or alkaline earth metal carbonates, may be mentioned as examples.

Among the compounds of the invention, those for which:

$R_2=R_4=$tert-butyl and $R_3=OH$, as well as those for which the substituted cinnamoyl group is attached at position b or c of the aromatic ring, are preferred.

The invention also encompasses the process for obtaining the compounds of formula (I), wherein a compound of formula (II):

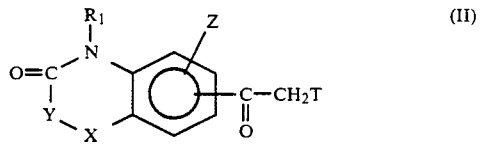

in which $R_1$, X, Y, Z and T have the same meaning as in the formula (I), obtained as described below or in Patent Applications France 73/23,281, 89/05,655, 90/07,812, Europe 0,223,674 and Poland 85/784 (appl. 161,856, 11.04.73), and the publications Ann. Chim. (Rome) 1955, 45, 172; Eur. J Med. Chem. 89, 24, 5, 479-485; Ind. J. Chem. 1983, 22B, 1236; Bull. Chem. Soc. Jpn 79, 52(4), 1135-8, is reacted in an acidic organic medium with an aldehyde of formula (III):

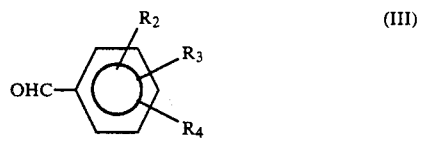

in which $R_2$, $R_3$ and $R_4$ have the same definition as in the formula (I), to lead, where appropriate after neutralization of the reaction medium, to a compound of formula (I), which is purified if necessary by a technique selected from chromatography and crystallization, the isomers of which, where applicable, are separated and which is salified, if so desired, when $R_1$ represents a hydrogen atom or at least one of the groups $R_2$, $R_3$ and $R_4$ represents a hydroxyl group, with a pharmaceutically acceptable base.

The compounds of formula (II) for which Z forms with T a link $-(CH_2)_n-CH(E)-$ or $-(CH_2)_n-CH(CH_2E')$, referred to as compounds (II/Z), with the exception of those for which X represents an oxygen atom, Y represents a single bond and E represents a methyl group (E' represents a hydrogen atom), are new and form part of the invention in the same way as the compounds of formula (I) for which they constitute synthesis intermediates.

The compounds of formula (II/Z) may be prepared by cyclization in an acidic medium of compounds of formula (IV), which are not necessarily isolated,

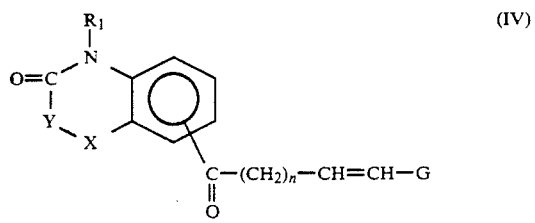
(IV)

with n, Y, X and $R_1$ having the same definition as in the formula (I) and G represents E or $CH_2E'$, which compound of formula (IV) will be obtained, either, when Y represents a single bond, by acylation in an acidic medium of a compound of formula (V):

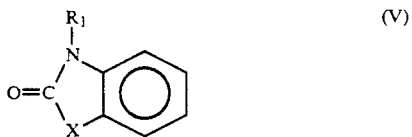
(V)

in which $R_1$ and X have the same definition as in the formula with an acid chloride of formula (VI):

$$ClOC-(CH_2)_nCH=CH-E \qquad (VI)$$

in which n and E have the same definition as in the formula (I), or with a compound of formula (VII):

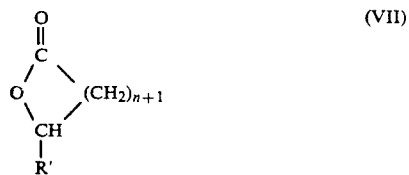
(VII)

in which n and E' have the same definition as in the formula (I), or, when n=0 by condensation of a compound of formula (VIII):

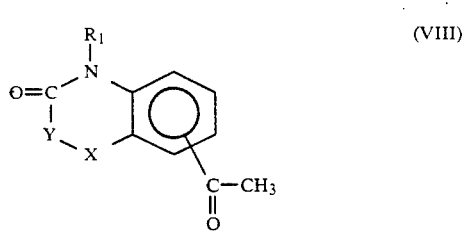
(VIII)

where X, Y, $R_1$ and n have the same definition as in the formula (I), obtained according to conventional means described in the literature, with an aldehyde of formula (IX):

$$G-CHO \qquad (IX)$$

where G has the same definition as above, or, when G represents a hydrogen atom and n is 0, by dehydrohalogenation in an alkaline medium of a compound of formula (X):

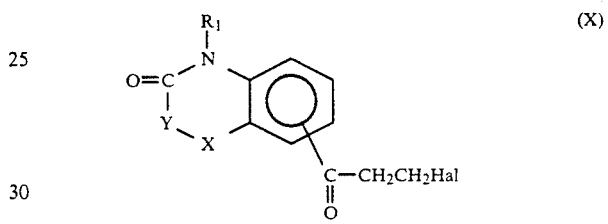
(X)

where $R_1$, X, Y and n have the same definition as above and Hal represents a halogen atom, where applicable with purification and/or separation of the The compounds of formula (I) possess advantageous pharmacological properties.

A pharmacological study of the compounds of the invention showed, in effect, that they were of low toxicity and endowed with a good level of anti-inflammatory activity, but most especially with exceptional antioxidant properties. This spectrum of activity renders the compounds of the present invention advantageous in a number of indications such as rheumatic pain, lumbosciatic neuralgia and cervicobrachial neuralgia, but most especially the prevention of acute peripheral arterial and cerebrovascular ischemic events and infarctions, in the prevention and treatment of platelet disorders, in atherosclerosis, in hypercholesterolemia and hypertriglyceridemia and in non-insulin-dependent diabetes as well as the multifarious complications such as cataracts, visual disorders, neuropathies and nephropathies. The antioxidant property of the compounds of the invention also enables them to be used as a preservative, in particular for organs.

Although some of the indications for the compounds of the invention are comparable to that in some documents of the prior art (Patent Application EP 0,223,674 in particular), the compounds of the invention are distinguished by a mode of action which is completely different and, in the final analysis, complementary. The compounds of Application EP 0,223,674 which are structurally very close to the compounds of the invention have proved, in effect, to be inactive in virtually all of the tests which demonstrate the excellent antioxidant power of the compounds of the invention.

The subject of the present invention is also pharmaceutical compositions containing the products of formula (I) or one of their addition salts with a pharmaceutically acceptable base, alone or in combination with one or more pharmaceutically acceptable, non-toxic, inert excipients or vehicles.

Among the pharmaceutical compositions according to the invention, there may be mentioned, more especially, those which are suitable for oral, parenteral and nasal administration, simple or sugar-coated tablets, sublingual tablets, sachets, packets, hard gelatin capsules, sublingual preparations, troches, suppositories, creams, ointments, skin gels, and the like.

The appropriate dosage varies according to the patient's age and weight, the administration route and the nature of the therapeutic indication or of any associated treatments, and ranges between 0.1 centigram and 4 grams per 24 hours.

PREPARATION 1

2,3-dihydro-2,7-dioxo-5-phenylcyclopenta[f]benzoxazole 1000 g of polyphosphoric acid are placed in a 1000-ml round-bottomed flask equipped with a mechanical stirrer. 119.36 g (0.45 mol) of 6-cinnamoylbenzoxazolinone, described in Application FR 73/23,281, are dissolved with stirring at a temperature of 120° C., and stirring is continued for 55 min while this temperature is maintained. The reaction mixture is hydrolyzed by vigorous stirring in 5 volumes of ice-cold water, and the product is drained, washed with water until the washes are neutral and dried. The precipitate obtained, finely powdered, is suspended in chloroform and the mixture is brought to the boil for 2 hours.

The mixture is filtered and the chloroform is then evaporated off on a water bath under vacuum. The operation is repeated several times. The evaporation residue is dissolved in 300 ml of absolute alcohol and evaporated again. The product is recrystallized in absolute alcohol.

Yield: 30%
Melting point: 229°-231° C.

PREPARATION 2

3-methyl-2,3-dihydro-2,7-dioxo-5-phenylcyclopenta[f]benzoxazole

The procedure used is that described in Preparation 1, replacing 6-cinnamoylbenzoxazolinone by 3-methyl-6-cinnamoylbenzoxazolinone.

Yield: 55%
Melting point: 161° C.

PREPARATION 3

3-methyl-6-penten-2-oylbenzoxazolinone

A mixture of 0.01 mol of 3-methyl-6-acetylbenzoxazolinone and 0.01 mol of propionaldehyde is stirred in 10% methanolic potassium hydroxide solution. The reaction medium is poured into water. The product is drained, washed to neutrality, dried and recrystallized in a suitable solvent.

PREPARATION 4

2,3-dihydro-2,7-dioxo-5-ethylcyclopenta[f]benzoxazole

Using the procedure described in Preparation 1, but replacing 6-cinnamoylbenzoxazolinone by 3-methyl-6-penten-2-oylbenzoxazolinone, the product of the title is obtained.

PREPARATION 5

3-methyl-6-acryloylbenzoxazolinone

In a 150-ml ground-necked flask equipped with a reflux condenser, 5 g (0.02 mol) of 3-methyl-6-(3-chloropropionyl)benzoxazolinone, described in Patent Application FR 89/02554, are dissolved in 70 ml of dimethylformamide. 2.04 g of potassium acetate are introduced. The mixture is heated with magnetic stirring to 75°-80° C. for 50 min. After cooling, the reaction mixture is poured into ice-cold water. The resulting mixture is stirred for 0.5 h. The precipitate obtained is drained, washed with water, dried and recrystallized in toluene.

Yield: 80%
Melting point: 145° C.

PREPARATION 6

2,3-dihydro-2,7-dioxo-3-methylcyclopenta[f]benzoxazole 0.03 mol of 6-acryloyl-3-methylbenzoxazolinone is dissolved in 30 $cm^3$ of concentrated (98%) sulfuric acid. The mixture is brought to a temperature of 40° C. for 4 hours with magnetic stirring. The reaction medium is cooled and poured into 150 $cm^3$ of ice-cold water. The precipitate formed is drained, washed with water until the filtrate is neutral, dried and recrystallized.

PREPARATION 7

2,3-dihydro-3,8-dioxo-4-methyl-6-phenyl-4H-cyclopenta]g][1,4]benzoxazine

Using the procedure described in Preparation 1, but replacing 6-cinnamoylbenzoxazolinone by 7-cinnamoyl-4-methyl-2,3-dihydro-4H-1,4-benzoxazin-3-one described in Patent Application EP 0,223,674, the product of the title is obtained.

PREPARATION 8

2,3-dihydro-4-methyl-7-cinnamoyl-4H-1,4-benzothiazine-3-one

Using the procedure described in Preparation 3, but replacing 3-methyl-6-acetylbenzoxazolin-3-one by 4-methyl-7-acetyl-2,3-dihydro-4H-1,4-benzothiazin-3-one and propionaldehyde by benzaldehyde, the product of the title is obtained.

PREPARATION 9

2,3-dihydro-4-methyl-2-benzyl-7-cinnamoyl-4H-benzoxazine-3-one

The following are prepared successively from 3-methyl-6-cinnamoylbenzoxazolinone:
2-methylamino-5-cinnamoylphenol by alkaline hydrolysis,
then, according to the protocol described in Patent Application EP 0,223,674 and using ethyl 2-bromo-3-phenylpropionate, the product of the title is obtained.

PREPARATION 10

2,3-dihydro-3,8-dioxo-4-methyl-6-phenyl-4H-cyclopenta[g][1,4]-benzothiazine

Using the procedure described in Preparation 1, but replacing 6-cinnamoylbenzoxazolinone by 2,3-dihydro-4-methyl-7-cinnamoyl-4H-1,4-benzothiazin-3-one obtained in Preparation 8, the product of the title is obtained.

PREPARATION 11

2,3dihydro-2-benzyl-3,8-dioxo-4-methyl-6-phenyl-4H-cyclopenta[g][1,4]benzoxazine Using the procedure described in Preparation 1, but replacing 6-cinnamoylbenzoxazolinone by 2,3-dihydro-2-benzyl-4-methyl-7-cinnamoyl-4H-1,4-benzoxazin-3-one described in Preparation 9, the product of the title is obtained.

The examples which follow illustrate the invention and in no way limit the latter.

EXAMPLE 1

5-(3',5'-di-tert-butyl-4'-hydroxycinnamo-yl)-3-methyl-benzoxazolinone 0.02 mol of 5-acetyl-3-methylbenzoxazolinone in 300 ml of ethanol saturated with hydrochloric acid is placed in a 500-ml ground-necked flask equipped with a stirrer.

0.02 mol of 3,5-di-tert-butyl-4-hydroxybenzaldehyde is added slowly and with stirring.

The reaction medium is left stirring at room temperature for two hours. The precipitate formed is drained and washed with water until the filtrate is neutral.

Recrystallization solvent: toluene
Yield: 86%
Melting point: 246°–248° C.

| | Elemental analysis: | | |
|---|---|---|---|
| | C | H | N |
| Calculated: | 73.68 | 7.17 | 3.43 |
| Found: | 73.66 | 7.19 | 3.41 |

Spectral characteristics:
Infrared:
3520 cm$^{-1}$:ν OH
1785 cm$^{-1}$: ν CO (O—CO—N)
Nuclear magnetic resonance (Solvent DMSO-d$_6$):
δ: 1.44 ppm, singlet, 18H (2.C(CH$_3$)$_3$)
δ: 3.44 ppm, singlet, 3H, N-CH$_3$

EXAMPLE 2

5-(3',5'-di-tert-butyl-4'-hydroxycinnamoyl)benzoxazolinone

The procedure used is that described in Example 1, replacing 5-acetyl-3-methylbenzoxazolinone by 5-acetylbenzoxazolinone. After two hours' stirring, the reaction medium is evaporated on a water bath under vacuum, the residue is taken up with water and the precipitate is stirred for a further hour, washed with water and dried.

Recrystallization solvent: toluene
Yield: 70%
Melting point: 206°–207° C.

| | Elemental analysis: | | |
|---|---|---|---|
| | C | H | N |
| Calculated: | 73.26 | 6.98 | 3.55 |
| Found: | 73.27 | 7.06 | 3.48 |

Spectral characteristics:
Infrared:
3610 cm$^{-1}$:ν OH
1780 cm$^{-1}$:ν CO (O—CO—N)
1650 cm$^{-1}$:ν CO (acyl)
1615 cm$^{-1}$:ν C═C (ethylenic)
Nuclear magnetic resonance (Solvent DMSO-d$_6$)
δ: 1.45 ppm, singlet, 18H (2.C(CH$_3$)$_3$)
δ: 5.62 ppm, signal with appearance of singlet, 1H, OH
δ: 9.77 ppm, signal with appearance of singlet, 1H, NH

EXAMPLE 3

6-(3',5'-de-tert-butyl-4'-hydroxycinnamoyl)benzothiazolinone

Using the procedure described in Example 2, but replacing 5-acetylbenzoxazolinone by 6-acetylbenzothiazolinone, the product of the title is obtained.
Recrystallization solvent: acetonitrile
Yield: 65%
Melting point: 262°–264°

| | Elemental analysis: | | | |
|---|---|---|---|---|
| | C | H | N | O |
| Calculated: | 70.38 | 6.65 | 3.42 | 11.72 |
| Found: | 70.42 | 6.68 | 3.25 | 11.94 |

Spectral characteristics:
Infrared:
3600 cm$^{-1}$:ν OH
3150 cm$^{-1}$:ν NH
1700 cm$^{-1}$:ν CO (S—CO—N)
1645 cm$^{-1}$:ν CO (ketonic)
Nuclear magnetic resonance (Solvent CDCl$_3$):
δ: 2.10 ppm, singlet, 18H (2.C(CH$_3$)$_3$)
δ: 5.60 ppm, singlet, 1H, OH
δ: 7.32 ppm, doublet, 1H, COCH, J=16Hz
ε: 7.85 ppm, doublet, 1H, COCH═CH, J=16Hz

EXAMPLE 4

6-(3',5'-di-tert-butyl-4'-hydroxycinnamoyl)-3-methyl-benzothiazolinone

Using the procedure described in Example 1, and replacing 5-acetyl-3-methylbenzoxazolinone by 6 -acety1- 3-methylbenzothiazolinone, the product of the title is obtained.
Recrystallization solvent: acetone
Yield: 77%
Melting point: 230°–232° C.

| | Elemental analysis: | | |
|---|---|---|---|
| | C | H | N |
| Calculated: | 70.88 | 6.90 | 3.31 |
| Found: | 71.01 | 6.90 | 3.20 |

Spectral characteristics:
Infrared:
3520 cm$^{-1}$:ν OH
1690 cm$^{-1}$:ν CO (NCOS)
1650 cm$^{-1}$:ν CO (ketonic)
Nuclear magnetic resonance (Solvent CDCl$_3$):
δ: 1.50 ppm, singlet, 18H (2.C(CH$_3$)$_3$)
δ: 3 50 ppm, singlet, 3H, N—CH$_3$
δ: 7.35 ppm, doublet, 1H, CO—CH, J=15.7Hz.
δ: 7.85 ppm, doublet, 1H, CO—CH═CH, J=15.7Hz

EXAMPLE 5

6-(3',5'-di-tert-butyl-4'-hydroxycinnamoyl)-3-methyl-benzoxazolinone

The procedure used is that described in Example 1 but, by replacing 5-acetyl-3-methylbenzoxazolinone by 6-acetyl-3-methylbenzoxazolinone, the product of the title is obtained.

Recrystallization solvent: acetone
Melting point: 21°-215° C.

|  | Elemental analysis: | | |
| --- | --- | --- | --- |
|  | C | H | N |
| Calculated: | 73.68 | 7.17 | 3.43 |
| Found: | 73.87 | 7.15 | 3.40 |

Spectral characteristics: In agreement with the structure

EXAMPLE 6

6-(3',540-di-tert-butyl-4'-hydroxycinnamoyl)benzoxazolinone

The procedure used is that described in Example 2 but, by replacing 5-acetylbenzoxazolinone by 6-acetyl-benzoxazolinone, the product of the title is obtained.
Melting point: 215° C.
Spectral characteristics: In agreement with structure

EXAMPLE 7

7-(3',54--di-tert-butyl-4'-hydroxycinnamoyl)-1,4-benzoxazin-3-one

Using the procedure described in Example 2, but replacing 5-acetylbenzoxazolinone by 7-acetyl-1,4-benzoxazin-3-one, the product of the title is obtained.
Recrystallization solvent: methanol
Melting point: 222° C.

|  | Elemental analysis: | | | |
| --- | --- | --- | --- | --- |
|  | C | H | N | O |
| Calculated: | 73.68 | 7.17 | 3.43 | 15.70 |
| Found: | 73.17 | 7.34 | 3.39 | 16.00 |

Spectral characteristics: In agreement with the structure

EXAMPLE 8

4-methyl-7-(3',5'-di-tert-butyl-4'-hydroxycinnamoyl)-1,4-benzoxazin-3-one

Using the procedure described in Example 1, but replacing 5-acetyl-3-methylbenzoxazolinone by 7-acetyl-3-methyl-1,4-benzoxazinone, the product of the title is obtained.
Recrystallization solvent: methanol
Melting point: 174-176° C.

|  | Elemental analysis: | | |
| --- | --- | --- | --- |
|  | C | H | N |
| Calculated: | 74.08 | 7.41 | 3.32 |
| Found: | 73.82 | 7.51 | 3.39 |

Spectral characteristics: In agreement with the structure

Using the procedures described in the preceding examples, and replacing 3,5-di-tert-butyl-4-hydroxybenzaldehyde by 3,4,5-trimethoxybenzaldehyde, the following are obtained, respectively:

EXAMPLE 9

5-(3',4',5'-trimethoxycinnamoyl)-3-methylbenzoxazolinone

EXAMPLE 10

5-(3',4',5'-trimethoxycinnamoyl)benzoxazolinone

EXAMPLE 11

6-(3',4',540-trimethyoxycinnamoyl)benzoxazolinone

EXAMPLE 12

6-(3',4',5'-trimethoxycinnamoyl)-3-methylbenzoxalinone

EXAMPLE 13

6-(3',4',540-trimethoxycinnamoyl)-3-methylbenzoxazolinone

EXAMPLE 14

6-(3',4',5'-trimethoxycinnamoyl)benzoxazolinone

EXAMPLE 15

7-(3',4',5'-trimethoxycinnamoyl)-1,4-benzoxazin-3-one

EXAMPLE 16

4-METHYL-7-(3',4',540-trimethoxycinnamoyl)-1,4-benzoxazin-3-one

By replacing 5-acetyl-3-methylbenzoxazolinone in Examples 1 and 9 by:
7-acetyl-2,4-benzoxazin-3-one, the following are obtained:

EXAMPLE 17

7-(3',5'-di-tert-butyl-4'-hydroxycinnamoyl)-2,4-benzoxazin-3-one

EXAMPLE 18

7-(3',4',5'-trimethoxycinnamoyl)-2,4-benzoxazin-3-one

By replacing 5-acetyl-3-methylbenzoxazolinone in Examples 1 and 9 by:
7-acetyl-2,4-benzothiazin-3-one, the following are obtained:

EXAMPLE 19

7-(3',5'-di-tert-butyl-4'-hydroxycinnamoyl)-2,4-benzothiazin-3-one

EXAMPLE 20

7-(3',4',5'-trimethoxycinnamoyl)-2,4-benzothiazin-3-one

By replacing 5-acetyl-3-methylbenzoxazolinone in Examples 1 and 9 by:
7-acetyl-1,4-benzothiazin-3-one described in Ann. Chim. (Rome) 1955, 45, 1972, the following are obtained:

EXAMPLE 21:

7-(3',5'-di-tert-butyl-4'-hydroxycinnamoyl)-1,4-benzothiazin-3-one

EXAMPLE 22

7-(3',4',5'-methoxycinnamoyl)-1,4-benzothiazin-3-one

By replacing 5-acetyl-3-methylbenzoxazolinone in Examples 1 and 9 by:

7-acetyl-2-methyl-1,4-benzoxazin-3-one, the following are obtained:

EXAMPLE 23

7-(3',5'-di-tert-butyl-4'-hydroxycinnamoyl)-2-methyl-1,4-benzoxazin-3-one

EXAMPLE 24

7-(3',4',5'-trimethoxycinnamoyl)-2-methyl-1,4-benzoxazin-3-one

By replacing 5-acetyl-3-methylbenzoxazolinone in Examples 1 and 9 by:
7-acetyl-2,2-dimethyl-1,4-benzoxazin-3-one, the following are obtained:

EXAMPLE 25

7-(3',540-di-tert-butyl-4'-hydroxycinnamoyl)-2,2-dimethyl-1,4-benzoxazin-3-one

EXAMPLE 26

7-(3',4',5'-trimethoxycinnamoyl)-2,2-di-methyl-1,4-benzoxazin-3-one

EXAMPLE 27

2,3-dihydro-3,5-dimethyl-6-(3',5'-di-tert-butyl-4'-hydroxybenzylidene)cyclopenta[f]benzoxazone-2,7-dione Using the procedure described in Example 1, but replacing 5-acetyl-3-methylbenzoxazolinone by 2,3-dihydro-3,5-dimethylcyclopenta[f]benzoxazole-2,7-dione described in French Patent Application 90/07,812, the product of the title is obtained.
Recrystallization solvent: toluene
Melting point: 217°–218° C.

EXAMPLE 28

2,3-dihydro-3,8-dimethyl-6-(3',5'-di-tert-butyl-4'-hydroxybenzylidene)cyclohexa[f]benzoxazone-2,5-dione Using the procedure described in Example 1, but replacing
5-acetyl-3-methylbenzoxazolinone by 2,3-dihydro-3,8-dimethylcyclohexa[f]benzoxazole-2,5-dione described in Patent Application France 90/07,812, the product of the title is obtained.
Recrystallization solvent: ethanol 90° strength
Melting point: 228°–229° C.

EXAMPLE 29

2,3-dihydro-3,7-dimethyl-6-(3',5'-di-tert-butyl-4'-hydroxybenzylidene)cyclopenta[f]benzoxazole-2,5-dione Using the procedure described in Example 1, but replacing 5-acetyl-3-methylbenzoxazolinone by 2,3-dihydro-3,7-dimethylcyclopenta[f]benzoxazole-2,5-dione described in Patent Application France 90/07,812, the product of the title is obtained.
Recrystallization solvent: toluene
Melting point: >270° C.

EXAMPLES 30 to 32

Using the procedures described in Examples 27 to 29, but replacing 3,5-di-tert-butyl-4-hydroxybenzaldehyde by 3,4,5-trimethoxybenzaldehyde, the following are obtained:

EXAMPLE 30

2,3-dihydro-3,5-dimethyl-6-(3',4',5'-trimethoxybenzylidene)cyclopenta[f]benzoxazole-2,7-dione

EXAMPLE 31

2,3-dihydro-3,8-dimethyl-6-(3',4',5'-trimethoxybenzylidene)cyclohexa[f]benzoxazole-2,5-dione

EXAMPLE 32

2,3-dihydro-3,7-dimethyl-6-(3',4'5'-trimethoxybenzylidene)cyclopenta[f]benzoxazole-2,5-dione

EXAMPLE 33

2,3-dihydro-5-methyl-6-(3',5'-di-tert-butyl-4'-hydroxybenzylidene)cyclopenta[f]benzoxa-zone-2,6-dione Using the procedure described in Example 1, but replacing 5-acetyl-3-methylbenzoxazolinone by 2,3-dihydro-5-methylcyclopenta[f]benzoxazole-2,7-dione, the product of the title is obtained.
Melting point: above 260° C.

EXAMPLE 34

2,3-dihydro-8-methyl-6-(3',5'-di-tert-butyl-4'-hydroxybenzylidene)cyclopenta[f]benzoxazole-2,5-dione Using the procedure described in Example 1, but replacing 5-acetyl-3-methylbenzoxazolinone by 2,3-dihydro-8-methylcyclohexa[f]benzoxazole-2,5-dione described in Patent Application FR 90/07,812, the product of the title is obtained.
Melting point: 228°–229° C.

EXAMPLE 35

2,3-dihydro-5-phenyl-6-(3',5'-di-tert-butyl-4'-hydroxybenzylidene)cyclopenta[f]benzoxazole-2,7-dione Using the procedure described in Example 1, but replacing 5-acetyl-3-methylbenzoxazolinone by 2,3-dihydro-5-phenylcyclopenta[f]benzoxazole-2,5-dione obtained in Preparation 1, the product of the title is obtained.
Reaction time: 15 hours
Recrystallization solvent: toluene
Melting point: above 260° C.
Spectral characteristics: $^1$H NMR
$\delta = 1.28$ ppm, singlet, 18H, 2.C(CH$_3$)$_3$

EXAMPLE 36

2,3-dihydro-3-methyl-5-phenyl-6-(3',5'-di-tert-butyl-4'-hydroxybenzylidene)cyclopenta[f]benzoxazole-2,7-dione Using the procedure described in Example 1, but replacing 5-acetyl-3-methylbenzoxazolinone by 2,3-dihydro-3-methyl-5-phenylcyclopenta[f]benzoxazole-2,7-dione obtained in Preparation 2, the product of the title is obtained.
Reaction time: 15 hours
Recrystallization solvent: toluene/cyclohexane (1:1)
Melting point: 229°–230° C.
Spectral characteristics: $^1$H NMR,
$\delta = 1.33$ ppm, singlet, 18H, 2.C(CH$_3$)$_3$

EXAMPLE 37

6-(3',5'-di-tert-butyl-4'-hydroxycinnamoyl)-1 4-benzothiazin-3-one

Using the procedure described in Example 1, but replacing -acetyl-3-methylbenzoxazolinone by 6-acetyl- 1,4-benzothiazin-3-one described in Indian J. Chem. 1983, 22B, 1236, the product of the title is obtained.

EXAMPLE 38

8-(3',5'-di-tert-butyl-4'-hydroxycinnamoyl)-1,4-benzothiazin-3-one

Using the procedure described in Example 1, but replacing i0 5-acetyl-3-methylbenzoxazolinone by 8-acetyl-1,4-benzothiazin-3-one described in the publication Eur. J. Med. Chem., 89, 24, 5, 483, the product of the title is obtained.

EXAMPLE 39

2,3-dihydro-3-methyl-5-ethyl-6-(3',5'-di-tert-butyl-4'-hydroxycinnamoyl)CYCLOPENTA[f]benzoxazole-2,7-dione Using the procedure described in Example 1, but replacing 5-acetyl-3-methylbenzoxazolinone by 2,3-dihydro-2,7-dioxo-5ethylcyclopenta[f]benzoxazole-2,7-dione, the product of the title is obtained.

EXAMPLE 40

2,3-dihydro-3-methyl-2,7-dioxo-6-(3',5'-di-tert-butyl-4'-hydroxybenzylidene)cyclopenta[f]benzoxazole-2,7-dione Using the procedure described in Example 1, but replacing 5-acetyl-3-methylbenzoxazolinone by 2,3-dihydro-2,7-dioxo-3-methylcyclopenta[f]benzoxazole obtained in Preparation 6, the product of the title is obtained.

EXAMPLE 41

2,3-dihydro-3,8-dioxo-4-methyl-6-phenyl-7-(3',5'-di-tert-butyl-4'-hydroxybenzyl-idene)-4H-cyclopenta[g][1,4]benzoxazine Using the procedure described in Example 1, but replacing 5-acetyl-3-methylbenzoxazolinone by 2,3-dihydro-3,8-dioxo-4-methyl-6-phenyl-4H-cyclopenta[g][1,4]benzoxazole obtained in Preparation 7, the product of the title is obtained.

EXAMPLE 42

2,3-dihydro-3,8-dioxo-4-methyl-6-phenyl-7-(3',5'-di-tert-butyl-4'-hydroxybenzyl-idene)-4H-cyclopenta[g][1,4]benzothiazine Using the procedure described in Example 1, but replacing 5-acetyl-3-methylbenzoxazolinone by 2,3-dihydro-3,8-dioxo-4-methyl-6-phenyl-4H-cyclopenta[g][1,4]benzothiazine obtained in Preparation 11, the product of the title is obtained.

EXAMPLE 43

2,3-dihydro-3,8-dioxo-2-benzyl-4-methyl-6-phenyl-7-(3',5'-di-tert-butyl-4'-hydroxybenzylidene-4H-cyclopenta[f][1,4]-benzoxazine Using the procedure described in Example 1, but replacing 5-acetyl-3-methylbenzoxazolinone by 2,3-dihydro-3,8-dioxo-4-methyl-2-benzyl-6-phenyl-4H-cyclopenta[f][1,4]benzoxazine obtained in Preparation 10, the product of the title is obtained.

Using the procedures described in the preceding Examples and employing suitable starting materials which those skilled in the art will have no difficulty in obtaining by means of the procedures and the literature cited above, the following are obtained.

2,3-dihydro-3,8-dioxo-4-methyl-6-thienyl-7-(3',5'-di-tert-butyl-4'-hydroxybenzylidene)-4H-cyclopenta[g][1,4]benzoxazine 2,3-dihydro-2,7-dioxo-3-methyl-5-thienyl-6-(3',5'-di-tert-butyl-4'-hydroxybenzylidene)-3H-cyclopenta[f][1,4]benzoxazole 2,3-dihydro-2,7-dioxo-3-methyl-5-(3',5'-di-tert-butyl-4'-hydroxybenzylidene-3H-cyclopenta[g][1,3]benzoxazole 2,3-dihydro-3,9-dioxo-4,7-dimethyl-8-(3',5'-di-tert-butyl-4'-hydroxybenzylidene-4H-cyclopenta[h][1,4]benzoxazine 2,3-dihydro-3,8-dioxo-2,2,4,6-tetramethyl-7-(3',5'-di-tert-butyl-4'-hydroxybenzylidene)-4H-cyclopenta[g][1,4]benzoxazine 2,3-dihydro-3,8-dioxo-2,2,4,6-tetramethyl-7-(3',5'-di-tert-butyl-4'-hydroxybenzylidene)-4H-cyclopenta[g][1,4]benzothiazine 2,3-dihydro-3,8-dioxo-2,2,4,6-trimethyl-6-phenyl-7-(3',5'-di-tert-butyl-4'-hydroxybenzylidene)-4N-cyclopenta[g][1,4]benzothiazine 2,3-dihydro-3,8-dioxo-2,2,4,6-trimethyl-6-(3',5'-hydroxyphenyl)-7-(3',5'-di-tert-butyl-4'-hydroxybenzylidene)-4H-cyclopenta[g][1,4]benzothiazine 2,3-dihydro-3,8-dioxo-2,2,4,6-tetramethyl-7-(3',5'-di-tert-butyl-4'-hydroxybenzylidene)-4H-cyclopenta[g][1,4]benzothiazine 2,3-dihydro-5-phenyl-6-(3',5'-di-tert-butyl-4'-hydroxybenzylidene)-4H-cyclopenta[f]benzothiazole-2,7-dione

PHARMACOLOGICAL STUDY OF THE COMPOUNDS OF THE INVENTION

EXAMPLE A

Study of the Acute Toxicity

The acute toxicity was assessed after the oral administration of increasing doses (0.1, 0.25, 0.50, 0.75 and 1 g/kg) to batches of 5 mice (20±2 grams). The animals were observed at regular intervals during the first day and daily during 2 weeks following the treatment.

It is apparent that the compounds of the invention are completely non-toxic. No deaths are observed after administration of a dose of 1 g.kg-l. No disorders are noted after administration of this dose.

EXAMPLE B

Demonstration of a Peroxidation-Inhibiting Activity

A study of the capacity of the compounds of the invention to trap free OH. radicals was studied on rat brain homogenates
- on the one hand with respect to the spontaneous peroxidation of lipids,
- on the other hand with respect to peroxidation induced by the Fe++/ascorbate (10 $\mu$M/250 $\mu$M) system.

a/ Measurement of the Inhibition of Spontaneous Lipid Peroxidation

The rat brain homogenates are placed in the presence or absence of the test compounds for 60 minutes at 37° C. The intensity of lipid peroxidation in the presence and in the absence of the compounds of the invention is determined by the substances reacting with thiobarbituric acid, expressed in mmol of malondialdehyde, by a method derived from that of YAGI (K. YAGI, Biochem. Med. 1976, 15, 212-216).

b/ Measurement of the Inhibition of Induced Lipid Peroxidation

The methodology is identical, with the exception of the addition to the homogenate of the Fe++/ascorbate radical-inducing system.

The reference substances in both cases are probucol and vitamin E. Some compounds of the invention produce, in a test, an inhibition of lipid peroxidation greater than that of probucol, the commercially available compound most active in this field of activity, and greater than that of vitamin E which is renowned for its antioxidant properties. Thus, Examples 33, 34, 35, 36 and 40 bring about, at a concentration of $10^{-5}M$, an approximately 50% inhibition of spontaneous peroxidation. An identical concentration of probucol brings about a 37% inhibition. An identical concentration of vitamin E an 18% inhibition.

As regards the test of induced peroxidation, the compounds of Examples 33, 34, 35 and 36 at a concentration of $10^{-5}M$ bring about an inhibition in the region of 50%. That of Example 4 an inhibition in the region of 30%. By way of comparison, the inhibition produced in this test by a $10^{-5}M$ concentration of probucol is 27% and by a $10^{-5}M$ concentration of vitamin E 6%.

The compound MZ130 of Patent Application EP 0,223,674, Example 1 and compound 6 of table I of Patent Application FR 73/23,281 did not evince significant activity in these tests.

EXAMPLE C

Measurement of the Inhibition of Formation of Conjugated Dienes Formed by Free-Radical Activity This methodology consists in generating free OH- radicals in an emulsion of linoleic acid, by means of a system consisting of an $Fe^{2+}/Fe^{3+}$ mixture. The compounds of the invention intensely inhibit diene formation. At a $10^{-5}M$ concentration, the compounds of Examples 2, 6 and 7 inhibit diene formation by approximately 75%.

The compound of Example 36 inhibits diene formation by approximately 50%.

By way of comparison, at a concentration of $10^{-5}M$, probucol inhibits this formation by only 24%, and the compound MZ 130 of Application EP 0,223,674, Example 1 and compound 6 of table I of Application FR 73/23,281 have no significant action in this test.

EXAMPLE D

Measurement of the Level of LDL Oxidation

Under these conditions, free radicals are generated by Cu++ in a medium containing native LDL in the presence or absence of the test compounds. The reaction is stopped by adding 2,6-di-tert-butyl-4-methyl-phenol and EDTA to the reaction medium and the oxidation products are assayed by FPLC.

Each LDL preparation is tested with probucol as a reference, the activity of which is designated by the peroxidation value $i=1$.

The results for the test products are hence expressed relative to this activity of probucol:

$$i_x = \frac{D_x - D_{control}}{D_{probucol} - D_{control}}$$

D being the height of the peak of fraction 27/28 of the chromatogram; the sum of the oxidized fractions 27/28 and 31/32 is equal to 100.

For very active products, the oxidized fraction 27/28 disappears. This is the outcome observed with the products of Examples 27, 28, 29, 33, 34, 35 and 36.

By way of comparison, the product MZ 130 of Application EP 0,223,674, Example 1 and compound 6 of table I of Application FR 73/23,281 have no significant activity in this test.

EXAMPLE E

Measurement of AAPH-Induced Hemolysis

Human red cells are placed in the presence of AAPH (2,2'-azobis(2-amidinopropane hydrochloride), a generator of free radicals at a constant rate, and in the presence or absence of the test compounds for 30 minutes at 37° C. The optical density of the supernatant is measured at 403 nm against a control without AAPH. The percentage inhibition of hemolysis is calculated by comparison with 100% hemolysis obtained from the AAPH control.

The compounds of the invention proved capable of strongly inhibiting AAPH-induced hemolysis.

Thus, the compounds of Examples 2, 3, 5 and 6 inhibit to the extent of between 78 and 88% the hemolysis induced by AAPH at a concentration of $10^{-5}M$ By way of comparison, probucol at a concentration of $10^{-5}M$ produces only a 48% inhibition. The product MZ 130 of Application EP 0,223,674, Example 1 and compound 6 of table I of Application FR 73/23,281 have no significant activity in this test.

EXAMPLE F

Measurement of the Inhibitions of Lipoxygenase Activity

The lipoxygenase activity is measured using washed human polynuclear cells, in the presence and absence of the claimed compounds after activation by calcium (A 23/87). The leukotriene $B_4$ ($LTB_4$) produced is measured by radioimmunoassay (Gresele, P. et al. Biochem. Biophys. Res. Comm. 1986, 137, 334-342).

Thus, at a concentration of $10^{-5}M$, Example 1 inhibits lipoxygenase action by approximately 80%, and Examples 5, 35 and 36 by approximately 60%, whereas probucol used as a reference at a concentration of 10-5M brings about only a 44% inhibition.

EXAMPLE G

Study of the Hypoglycemic Activity

Male KK mice are placed in cages at the age of eight weeks. They are used for the experiment when their weight is higher than 40 grams at the age of 4-5 months.

The compound of the invention is suspended in acacia syrup. Each test compound is administered orally at a dose of 150 or 50 mg/kg, 18 hours before drawing a blood sample.

The blood is collected by drawing from the caudal vein into a hematocrit tube, and then centrifuged. The plasma is collected and an assay of the blood sugar level is performed.

It is apparent that the compounds of the invention significantly decrease the blood sugar level.

PHARMACEUTICAL COMPOSITION

Example

Tablets

Tablets containing 20 mg of 2,3-dihydro-3-methyl-5-phenyl-6-(3',540 -di-tert-butyl-4'-hydroxybenzylidene)-3H-cyclopenta[f]benzoxazole-2,7-dione

| Preparation formula for 1000 tablets: | |
|---|---|
| 2,3-Dihydro-3-methyl-5-phenyl-6-(3',5'-di-tert-butyl-4'-hydroxy benzylidene)-3H-cyclopenta[f]benzoxazole-2,7-dione | 20 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

What is claimed is:

1. A compound selected from those having the formula (I):

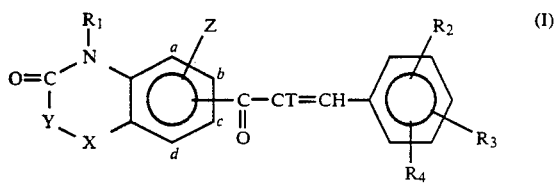

in which:

$R_1$ represents a hydrogen atom or a lower alkyl radical,

X represents:
an oxygen or sulfur atom,
a $CH_2$ group, on condition that, in this case,
Y represents an oxygen or sulfur atom, Y represents:
a single bond or a group $CR_7R_8$, where $R_7$ and $R_8$, which may be identical or different, represent, independently of one another, a hydrogen atom, a lower alkyl group, a phenyl group, a substituted phenyl group, a phenylalkyl group or a substituted phenylalkyl group,
an oxygen or sulfur atom, on condition that, in this case, X represents a $CH_2$ group, Z represents (1) a hydrogen atom, and in this case T also represents a hydrogen atom, or (2) Z forms with T a link $-(CH_2)_n-(CH(E)-$ or $(CH_2)_n-CH(CH_2E')$ with being n an integer equal to 0, 1, 2 or 3, which, in this case Z is carried by a carbon adjacent to the carbon carrying the acyl group, and E or E' represents a hydrogen atom, a lower alkyl group or a phenyl, thienyl or substituted phenyl group, the term "substituted" in relation to the terms phenyl and phenylalkyl in the definition of $R_7$ and $R_8$ and E and E' meaning that these groups may be substituted with one or more substituents selected from lower alkyl, lower alkoxy, halogen, trifluoromethyl or hydroxyl, $R_2$, $R_3$ and $R_4$, which may be identical or different, represent, independently of one another, a hydroxyl or lower alkoxy group or a lower alkyl group, its enantiomers, epimers and diastereoisomers as well as, when $R_1$ represents a hydrogen atom or when at least one of the groups $R_2$, $R_3$ and $R_4$ represents a hydroxyl group, its addition salts with a pharmaceutically acceptable base, on the lower alkyl or lower alkoxy being understood to mean linear or branched groups comprising from 1 to 6 carbon atoms.

2. A compound as claimed in claim 1 in which $R_3$ represents a hydroxyl group and $R_2$ and $R_4$ each simultaneously represent a tert-butyl group, its isomers and its addition salts with a pharmaceutically acceptable base.

3. A compound as claimed in claim 1 in which Z forms with T link $(CH_2)n-CH(E)$ or $(CH_2)_n-CH(CH_2E')$ with n being an integer equal to 0, 1, 2 or 3, in which case Z is carried by a carbon adjacent to the carbon carrying the acyl group, and E or E' represents a hydrogen atom, a lower alkyl group or a phenyl, thienyl or substituted phenyl group, its enantiomers, epimers and diastereoisomers as well as, when $R_1$ represents a hydrogen atom or when at least one of the groups $R_2$, $R_3$ and $R_4$ represents a hydroxyl group, its addition salts with a pharmaceutically acceptable base.

4. A compound as claimed in claim 1 in which Z and T simultaneously represent a hydrogen atom, its isomers as well as, when $R_1$ represents a hydrogen atom and at least one of the groups $R_2$, $R_3$ and $R_4$ represents a hydroxyl group, its addition salts with a pharmaceutically acceptable base.

5. A compound as claimed in claim 1 in which Y represents a single bond or a $CH_2$ group, its isomers as well as, when $R_1$ represents a hydrogen atom and at least one of the groups $R_2$, $R_3$ and $R_4$ represents a hydroxyl group, its addition salts with a pharmaceutically acceptable base.

6. A compound as claimed in claim 1 in which X represents an oxygen or sulfur atom, its isomers as well as, when $R_1$ represents a hydrogen atom and at least one of the groups $R_2$, $R_3$ and $R_4$ represents a hydroxyl group, its addition salts with a pharmaceutically acceptable base.

7. A compound as claimed in claim 3 in which E represents a phenyl group optionally substituted with one or more groups selected from hydroxyl and lower alkyl, its isomers and its addition salts with a pharmaceutically acceptable base.

8. A compound as claimed in claim 1 which is 7-(3',5'-di-tert-butyl-4'-hydroxycinnamoyl)-1,4-benzothiazin-3-one, its isomers and its addition salts with a pharmaceutically acceptable base.

9. A compound as claimed in claim 1 which is select from 6-(3',5'-di-tert-butyl-4'-hydroxycinnamoyl)benzoxazolinone, its isomers and its addition salts with a pharmaceutically acceptable base.

10. A compound as claimed in claim 1 which is select from 2,3-dihydro-5-phenyl-6-(3',5'-di-tert-butyl-4'-hydroxybenzylidene) cyclopenta[f]benzoxazole-2,7-dione, its isomers and its addition salts with a pharmaceutically acceptable base.

11. A compound as claimed in claim 1 which is select from 2,3-dihydro-3,8-dioxo-2,2,4-trimethyl-6-(3',5'-di-tert-butyl-4'-hydroxyphenyl)-7-(3',5'-di-tert-butyl-4'-hydroxybenzylidene)-4H-cyclopenta[g][1,4]benzothiazine, its isomers and its addition salts with a pharmaceutically acceptable base.

12. A compound as claimed in claim 1 which is select from 2,3-dihydro-3,8-dioxo-4-methyl-6-phenyl-7-(3',5'-di-tert-butyl-4'-hydroxybenzylidene)-4H-cyclopenta[g][1,4]benzothiazine, its isomers and its addition salts with a pharmaceutically acceptable base.

13. A compound as claimed in claim 1 which is select from 2,3-dihydro-3-methyl-5-phenyl-6-(3',5'-di-tert-butyl-4'-hydroxybenzylidene)cyclopenta[f]benzoxazole-2,7-dione, its isomers and its addition salts with a pharmaceutically acceptable base.

14. A compound as claimed in claim 1 which is select from 2,3-dihydro-5-phenyl-6-(3',5'-di-tert-butyl-4'-hydroxybenzylidene) cyclopenta[f]benzothiazole-2,7-dione, its isomers and its addition salts with a pharmaceutically acceptable base.

15. A pharmaceutical composition useful in treating hyperlipidemia involving oxidation of LDL containing as active principle an effective antoxidant amount of a compound as claimed in claim 1, in combination with a pharmaceutically-acceptable excipient or vehicle.

16. A method of treating a living animal afflicted with hyperlipidemia involving oxidation of LDL comprising the step of administering to the said living animal an effective for the alleviation of said condition.

17. An antioxidant pharmaceutical composition useful in the treatment of an ailment involving a free-radical aggression disorder containing as active antioxidant principle an effective antioxidant amount of a compound as claimed in claim 1, in combination with a pharmaceutically-acceptable excipient or vehicle.

18. A method of treating a living animal afflicted with an ailment involving a free-radical aggression disorder comprising the step of administering to the said living animal an amount of an antioxidant compound of claim 1 which is effective for alleviation of the said disorder.

* * * * *

UNITED STATES PATENT AND TRADEMARK OFFICE
CERTIFICATE OF CORRECTION

PATENT NO. : 5,179,091  Page 1 of 3

DATED : Jan. 12, 1993

INVENTOR(S) : Daniel Lesieur, Daniel H. Caignard, Isabelle Lesieur, Michelle Devissaguet, Béatrice Guardiola It is certified that error appears in the above-identified patent and that said Letters Patent is hereby corrected as shown below:

Title Page, [56] References Cited, U. S. PATENT DOCUMENTS,
   line 13; "Moussaviet should read -- Moussavi --

Column 2, line 8; "Or" should read -- or --.
Column 3, line 47; "formula with" should read --formula (I), with--.
Column 3, approximately line 63, in the formula VII; "R'" should read --E'--.
Column 4, line 35; "of the" should read -- of the isomers. --.
Column 7, line 5; "2,3dihydro-" should read -- 2,3-dihydro- --.
Column 8, approximately line 12; "5'-de-" should read -- 5'-di- --.
Column 8, approximately line 38; "ε : 7.85" should read -- δ:7.85 --.
Column 8, approximately line 45/46; move the "1-" at the beginning of line 46
   to the end of line 45 after "acety"
Column 9, approximately line 11; "21°-215° C." should read -- 210°-215° C.--.
Column 9, approximately line 22; "6-(3',540" should read --6-(3' ,5' --.
Column 9, approximately line 32; "7-(3',54-" should read --7-(3',5'--.
Column 10, line 14; "6-(3',4',540 -" should read --6-(3',4',5'- --
Column 10, line 14; "benzoxazolinone" should read --benzothiazolinone--.
Column 10, approximately line 16; "methylbenzoxali-none" should read
   -- methylbenzo-thiazolinone --.
Column 10, line 20; "6-(3',4',540" should read --6-(3',4',5' --.
Column 10, line 30; "7-(3',4',540" should read -- -7-(3',4',5' -- .
Column 10, approximately line 65; "methoxycinnamoyl" should read
   -- trimethoxycinnamoyl --.
Column 11, approximately line 18; "7-(3',540" should read -- 7-(3',5' --.
Column 11, line 40; "benzoxazone" should read -- benzoxazole --.
Column 12, approximately line 15; "zone-2,6-dione" should read
   -- zole-2,7-dione --.
Column 12, line 25; "cyclopenta" should read -- cyclohexa --.
Column 12, line 64; "-1" should read -- -1, --.
Column 12, line 68; "replacing -acetyl-" should read --replacing 5-acetyl- --.
Column 13, approximately line 9; "replacing i0 5-acetyl-" should read
   -- replacing 5-acetyl- --.
Column 13, approximately line 15; "hydroxycinnamoyl)CYCLOPENTA" should read
   -- hydroxybenzylidene)cyclopenta --.

UNITED STATES PATENT AND TRADEMARK OFFICE
CERTIFICATE OF CORRECTION

PATENT NO. : 5,179,091

DATED : Jan. 12, 1993

INVENTOR(S) : Daniel Lesieur, Daniel H. Caignard, Isabelle Lesieur, Michelle Devissaqauet Béatrice Guardiola It is certified that error appears in the above-identified patent and that said Letters Patent is hereby corrected as shown below:

Column 13, line 20; "5ethylcyclopenta" should read -- 5-ethylcyclopenta --.
Column 14, approximately line 9; "-4'-hydroxybenzylidene-" should read -- -4'-hydroxyphenyl)-6-(3',5'-di-tert-butyl-4'-hydroxybenzylidene)- -- .
Column 14, approximately line 12; "-hydroxybenzylidene-" should read -- hydroxybenzylidene)- --.
Column 14, approximately line 21; "-2,2,4,6-trimethyl-" should read -- -2,2,4-trimethyl- --.
Column 14, approximately line 22; "-4N-" should read -- -4H- --.
Column 14, line 25; "-2,2,4,6-trimethyl-" should read -- -2,2,4-trimethyl- --.
Column 14, line 25; "(3',5'-hydroxyphenyl)" should read --(3',5'-di-tert-butyl-4'-hydroxyphenyl) --.
Column 16, approximately line 41; "Inhibitions" should read -- Inhibition--.
Column 17, line 9; "540" should read -- 5' --.
Column 17, line 51; "atom, and in this case" should read -- atom, in which case --.
Column 17, line 54; "with being n an" should read -- with n being an --.

Column 17, line 55; "which, in this case" should read -- in which case --.

Column 18, line 6; delete "on the".
Column 18, approximately line 15; "T link" should read -- T a link --.
Column 18, approximately line 50; "is 7-" should read --is selected from 7- --.

Column 18, line 54/55; "is select from" should read -- is selected from --.

Column 18, line 58/59; "is select from" should read -- is selected from--.

Column 18, line 63/64; "is select from" should read -- is selected from--.

Column 19, line 11 ; "is select from" should read -- is selected from--.

UNITED STATES PATENT AND TRADEMARK OFFICE
CERTIFICATE OF CORRECTION

PATENT NO. : 5,179,091

DATED : Jan. 12, 1993

INVENTOR(S) : Daniel Lesieur, Daniel H. Caignard, Isabelle Lesieur, Michelle Devissaguet, Béatrice Guardiola It is certified that error appears in the above-identified patent and that said Letters Patent is hereby corrected as shown below:

Column 19, line 6/7; "is select from; should read -- is selected from--.

Column 19, line 11/12; "is select from" should read -- is selected from --.

Column 20, line 6; "effective for" should read -- effective antioxidant amount of a compound of claim 1 which is effective for --.

Signed and Sealed this

Fifteenth Day of November, 1994

Attest:

BRUCE LEHMAN

Attesting Officer  Commissioner of Patents and Trademarks